United States Patent
Khalil et al.

(10) Patent No.: US 9,283,042 B2
(45) Date of Patent: Mar. 15, 2016

(54) SCOPE PILLOW DRAPE WITH EXTENSION SHELF AND POWER CORD HOOK

(75) Inventors: Heidi Frances Khalil, Atlanta, GA (US); Raymond Wilson Tsang, Ashburn, VA (US); David Alan Daugherty, Columbus, MS (US); John Alan Gibson, Ethelsville, AL (US)

(73) Assignee: Ecolab USA Inc., St. Paul, MN (US)

( * ) Notice: Subject to any disclaimer, the term of this patent is extended or adjusted under 35 U.S.C. 154(b) by 231 days.

(21) Appl. No.: 13/609,963

(22) Filed: Sep. 11, 2012

(65) Prior Publication Data

US 2014/0069436 A1    Mar. 13, 2014

(51) Int. Cl.
*A61B 19/10*    (2006.01)
*A61B 19/02*    (2006.01)

(52) U.S. Cl.
CPC ........... *A61B 19/10* (2013.01); *A61B 2019/025* (2013.01)

(58) Field of Classification Search
USPC ......... 128/849–856, DIG. 15, 24; 383/33, 63, 383/65; 604/114, 357; 219/429–430, 433
See application file for complete search history.

(56) References Cited

U.S. PATENT DOCUMENTS

| | | | |
|---|---|---|---|
| 4,342,390 A * | 8/1982 | Mitchell et al. | 206/363 |
| 6,231,596 B1 | 5/2001 | Collins | |
| 6,884,970 B2 * | 4/2005 | Lehman | 219/432 |
| 7,350,373 B1 | 4/2008 | Faries, Jr. et al. | |
| 7,418,966 B2 | 9/2008 | Faries, Jr. et al. | |
| 7,448,099 B2 | 11/2008 | Abernathie | |
| 7,560,667 B2 | 7/2009 | Kammer et al. | |
| 7,671,302 B1 | 3/2010 | Faries, Jr. et al. | |
| 7,728,262 B1 | 6/2010 | Faries, Jr. et al. | |
| 8,074,815 B2 | 12/2011 | Gerstner | |
| 8,148,666 B2 * | 4/2012 | Faries et al. | 219/429 |
| 8,148,667 B2 | 4/2012 | Faries, Jr. et al. | |
| 2004/0118410 A1 * | 6/2004 | Griesbach et al. | 128/852 |
| 2012/0187104 A1 * | 7/2012 | Heymann et al. | 219/385 |

FOREIGN PATENT DOCUMENTS

WO    WO 2012/029049 A1    3/2012

OTHER PUBLICATIONS

Ecolab USA Inc., PCT/US2013/058011 filed Sep. 4, 2013, "Notification of Transmittal of The International Search Report and The Written Opinion of The International Searching Authority, or The Declaration" mailed Dec. 2, 2013.

* cited by examiner

*Primary Examiner* — Ophelia A Hawthorne
(74) *Attorney, Agent, or Firm* — McKee, Voorhees & Sease, PLC (57) ABSTRACT

A pillow drape for use with a thermal medical treatment apparatus or device is provided. The drape includes a sterilized sheet for covering the warming medical device that covers the device body and a basin that is used to store a warming liquid. The pillow drape includes an enclosure having a support member therein to support a medical instrument, such as a surgical scope, during warming of the scope. The support member can be housed between first and second sections of the pillow drape sheet in a pocket portion. The support member can be positioned on an extension shelf added to the warming device to provide additional storage room while not taking up room in the surgical or medical room. Additionally, a cord hook can be attached to the medical device to aid in routing a power cord for the device away from traffic.

18 Claims, 6 Drawing Sheets

SCOPE PILLOW DRAPE WITH EXTENSION SHELF AND POWER CORD HOOK

FIELD OF THE INVENTION

The present invention relates generally to a system or apparatus for thermally treating medical instruments. More particularly, but not exclusively, the invention relates towards an improved system and apparatus for covering a thermal medical treatment apparatus and for supporting a medical instrument being warmed by the thermal medical treatment apparatus.

BACKGROUND OF THE INVENTION

Surgical scopes (e.g., laparoscopes, endoscopes, arthroscopes, etc.) are used in corrective medical procedures, as well as in medical procedures that image interior viscera such as surfaces of the stomach, small intestines, and colon. The use of surgical scopes permits a surgeon to view a patient body interior with a minimal amount of cutting of patient tissue. The surgical scopes may be warmed prior to use, where scope optics must remain dry to protect those optics and prevent distortion of the image. The scopes are warmed for several reasons, including enhancing image results, preventing infections, and maintaining normothermia. For example, a scope that is not warmed prior to being inserted into a patient body may fog due to differences between the body temperature and scope temperature, thereby impeding or distorting the resulting image. Further, scopes may be warmed to minimize trauma caused to tissue in response to insertion of the scope into the patient body. The trauma basically results from the temperature difference between the scope and the tissue. Inserting a hot or cold scope may damage tissue, thereby leading to infections. Inserting a cold scope may also lower core body temperature, thereby leading to hypothermia and compromising patient safety.

Therefore, thermal warming systems or devices may warm the scopes. The thermal devices generally include a body or cabinet, and a basin or recess positioned within a top surface of the body. The basin is configured to contain and thermally treat a liquid bath. The medical instrument, or scope, is then placed in the thermally treated bath to raise the temperature of the insertion end of the scope to the desired temperature prior to inserting the scope into the patient. The opposite end, or optical end, of the scope is positioned outside of the bath so as to not damage the optics, which can be expensive to replace.

However, it should also be appreciated that the scopes and other medical instruments and devices must be sterile, so as to reduce the chance of infecting a patient during surgery or other procedures. Therefore, sterilized plastic sheets have been placed over the thermal warming systems, including the basis, to reduce the risk of infection. The liquid is added directly on the sheet in the basin, with additional parts of the sheet hanging over and around the device.

The medical scopes are often longer than the length of the basin and distance to an edge of the warming device. Thus, when the end of the scope is being warmed in the basin, the opposite end extends at an angle beyond the edge of the device, which increases the chance that the scope can fall out of the basin. Doing so can introduce the insertion end of the scope to potentially harmful bacteria, and can also damage the optic end of the scope, which, as noted above, can be rather expensive.

Methods have been taken by medical staff to reduce the chance that the scope will fall out of or off of the thermal device. For example, it is not uncommon for a surgical team to move a wheeled shelf adjacent the wheeled thermal device, such that the optic end of the scope can rest on the shelf, with the optic end elevated to ensure that the insertion end remains in the thermally treated liquid solution. However, doing so reduces the amount of shelf space available in the surgery room, and also introduces additional risks to the scope. An otherwise useful shelf must be used to support the scope, or an otherwise unneeded shelf must be used, which reduces the amount of space in the room. As both the second shelf and the thermal device are on wheels, they can be easily moved, even when not purposefully moved. Moving the second shelf, either purposefully or accidentally, will move the support of the scope, which can cause the scope to fall from the thermal device, introducing the problems discussed above.

Therefore, there is a need in the art for an apparatus and system that can be used with a thermal warming medical device or apparatus that covers the device to ensure a sterilized medical room. There is also a need for a medical drape or cover that includes a scope support member housed within to support a scope during warming of the scope in the medical device. Furthermore, there is a need for a shelf that can be attached to the medical device to increase the amount of usable space, while minimizing intrusion into the medical room space. The shelf can also be used to support the support member of the drape without having to use a separate wheeled shelf in the room.

SUMMARY OF THE INVENTION

Therefore, it is principal object, feature, and/or advantage of the present invention to provide an apparatus that overcomes the deficiencies in the art.

It is another object, feature, and/or advantage of the present invention to provide a thermal device drape that includes a support member for supporting a medical instrument that needs warmed or otherwise sterilized.

It is still another object, feature, and/or advantage of the present invention to provide a support member within a drape that includes various shapes to prevent medical instruments from rolling off the support.

It is a further object, feature, and/or advantage of the present invention to provide a drape and system for a warming medical device that includes a shelf for supporting a medical instrument support member for the warming device.

It is still a further object, feature, and/or advantage of the present invention to provide a system that includes a cord hook for redirecting and routing a power cord for a warming medical device.

It is yet a further object, feature, and/or advantage of the present invention to provide a system including a drape, support member, extension shelf, and hook to provide stability for a warming medical device while not reducing space in a medical room.

These and/or other objects, features, and advantages of the present invention will be apparent to those skilled in the art. The present invention is not to be limited to or by these objects, features and advantages. No single embodiment need provide each and every object, feature, or advantage.

According to one aspect of the present invention, a drape for use with a thermal medical treatment apparatus having a body including a recessed basin in a top surface is provided. The drape includes a sheet for covering the apparatus basin and body and hanging from the apparatus; and a support member housed in the sheet for supporting a medical device adjacent the basin.

According to another aspect of the present invention, a drape for use with a thermal medical treatment apparatus having a body including a recessed basin in a top surface is provided. The drape includes a first sheet for covering the apparatus basin and body and hanging from the apparatus; a second sheet attached to the first sheet to form a pocket therebetween; and a support member positioned in the pocket of the first and second sheets, the support member configured to support a medical device adjacent the basin.

According to yet another aspect of the present invention, a system for covering a thermal medical treatment apparatus having a body including a recessed basin in a top surface is provided. The system includes an extension shelf attached to the apparatus body adjacent the basin; a sheet covering the extension shelf, apparatus basin, and apparatus body and hanging therefrom; and a support member housed in the sheet and positioned on the extension shelf for supporting a medical device adjacent the basin.

The invention includes a pillow drape with extension shelf and power cord hook to offer improved stability of scopes during warming. The extension shelf is designed to offer increased working surface area of the warmer while minimizing intrusion into the operating room space. The power cord hook allows for power cord storage and convenient change of orientation relative to the sterile field. The pillow drape incorporates a foam holder to provide stable scope positioning during warming.

DETAILED DESCRIPTION OF THE PREFERRED EMBODIMENTS

Figure 1:
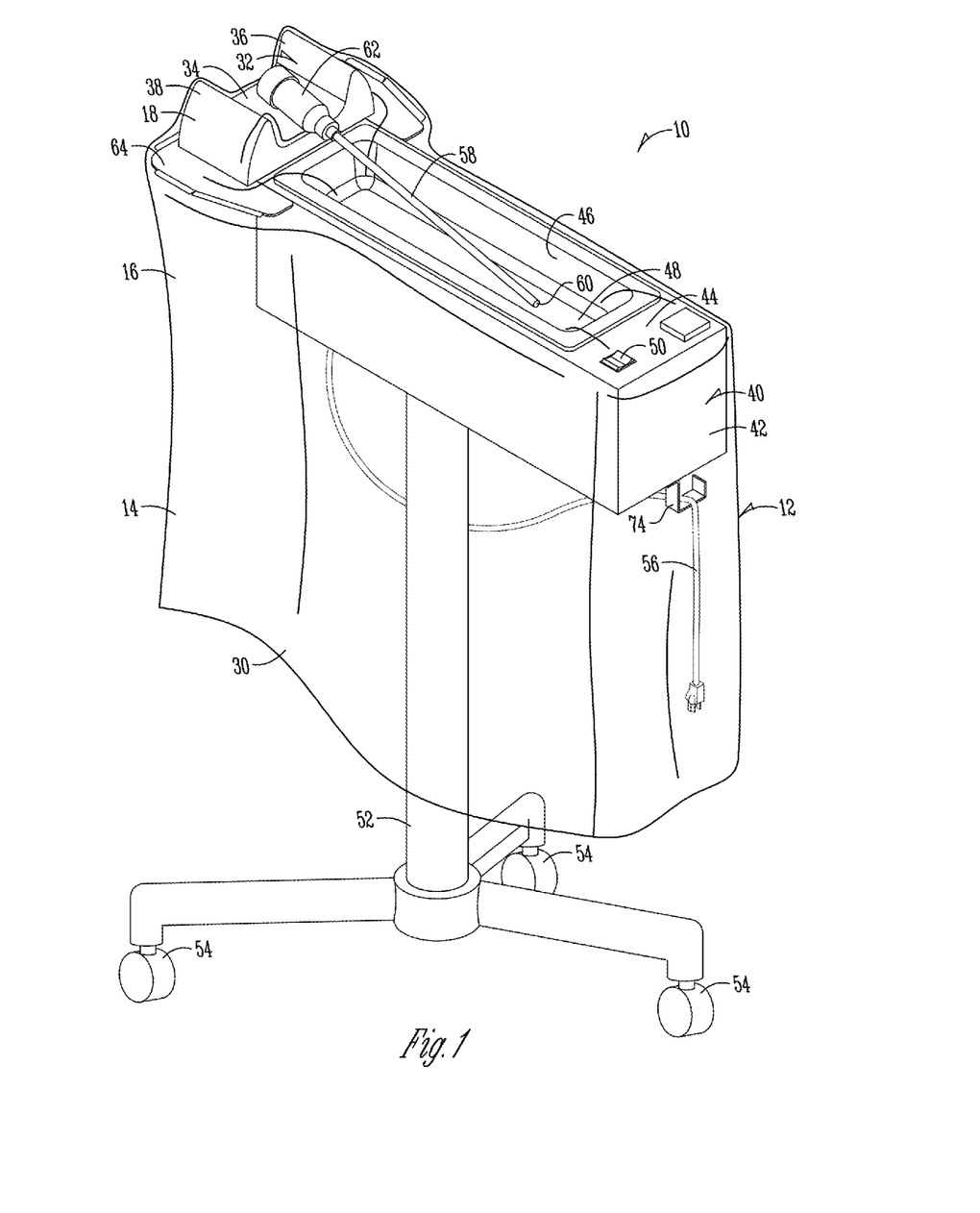
FIG. 1 is a perspective view of a medical warming device with a drape system attached and covering the same according to the present invention.
Figure 2:
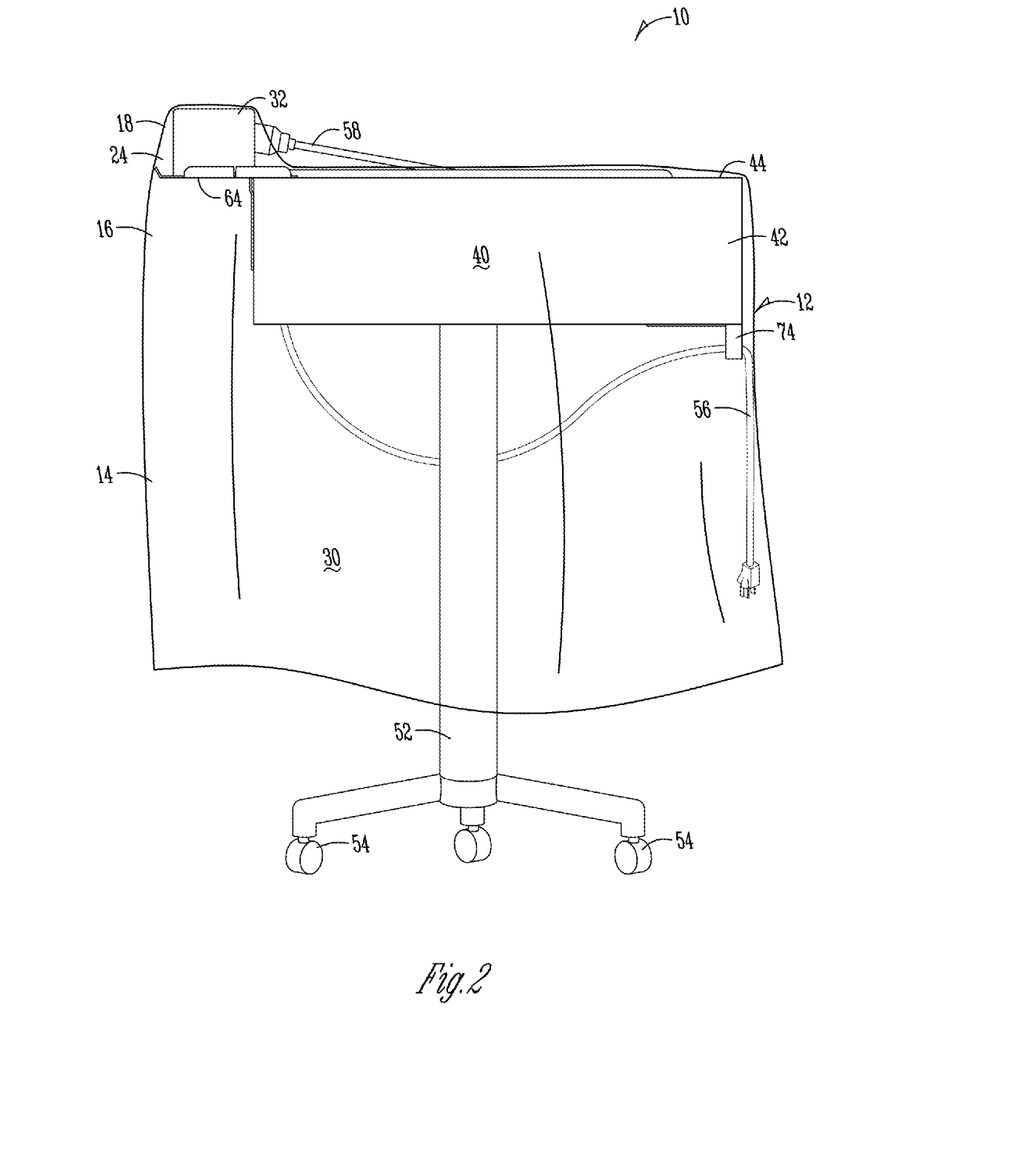
FIG. 2 is a side elevation view of the device and system of FIG. 1.
Figure 3:
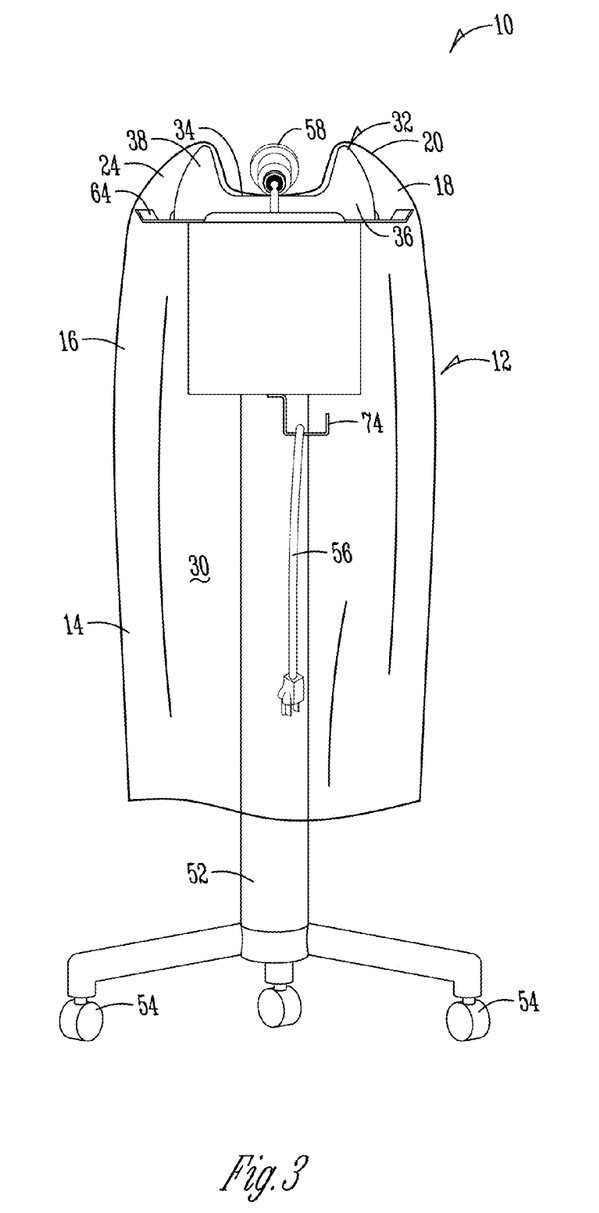
FIG. 3 is a front elevation view of the device and system of FIG. 1.

FIG. 1 is a perspective view of a medical warming device with a drape system attached thereto and covering the same, according to the present invention. As shown in FIG. 1, a medical system 10 includes, in part, a pillow drape 12 and a warming device 40. The warming device 40 is a medical apparatus used to warm scopes 58, such as surgical scopes (e.g., endoscopes or the like). The scopes 58 generally include an insertion end 60 and an optic end 62, which contains a camera or other optical device. However, as the insertion end 60 will be inserted into a patient, it is necessary to warm the insertion end 60 prior to insertion. Therefore, the scope 58 is placed in a liquid 48 contained in a basin 46 formed in a top surface 44 of the body 42 of the warming device 40. The insertion end 60 of the scope 58 can be warmed to a desired temperature prior to inserting the scope in the patient during surgery or other medical procedures. Furthermore, the warming device 40 may be attached to a stand 52 including a plurality of wheels 54 to move the warming device 40 as needed in the surgical or medical room.

In order to ensure a sterile environment in the surgical room, a sterilized pillow drape 12 is included to cover the warming device 40, including the basin 46. As shown in FIG. 1, the pillow drape 12 covers the warming device 40, and the liquid 48 is added on top of the sterilized pillow drape 12, and the scope 58 is then included in the warming device 40 to warm as needed.

An embodiment of the pillow drape 12 is shown in FIGS. 1-4. The pillow drape 12 includes generally a sheet 14, which may be a sterilized polyurethane sheet. It is contemplated that the sheet 14 be clear or be colored as needed or desired. The pillow drape 12 also includes a first section 16 and a second section 18. The first section 16 includes generally the sheet 14, which may also be known as a first sheet. The second section 18 includes a cover portion 20 defining a pocket 24 between the first and second sections. Housed within the pocket 24 is a support member 32. The support member 32, as shown in FIG. 1, can be used to support an end, shown to be the optic end 62, of the scope 58 in the warming device 40.

The support member 32 includes a surface 34 and first and second walls 36, 38 extending generally upwards from the first surface 34. The first and second walls 36, 38 aid in preventing the scope 58 from rolling off of the support member and warming device. However, it should be contemplated that the exact shape of the support member 32 need not be that shown in FIGS. 1-3, and that generally any shape may be used to aid in supporting the scope 58 in the warming device 40. The support member 32 may comprise generally any material capable of supporting the scope 58 in the warming device 40. However, according to one embodiment, a foam material is used. The density of the foam may vary according to the type of scope used, as well as other factors. The present invention contemplates that any density be used, and that the invention is not to be limited to any such densities.

Therefore, the support member 32 may be designed and cut out of a bulk piece of foam to the desired shape for the pillow drape 12. The size of the support member 32 may be adjusted and configured as necessary. For example, in some situations, multiple scopes will be needed to be warmed in the warming device at the same time. Therefore, the present invention contemplates that a generally wider support member 32 (wider surface 34) be used to support the plurality of scopes. Furthermore, it is contemplated that the support member 32 of the present invention comprises a generally pliable or deformable material such that the resting of the scope 58 on the support member 32 will cause a surface of the support member to slightly deform. The deformation of the support member 32 due to the weight of the scope will further aid in preventing the accidental falling of the scope from the warming device 40, while also providing a surface that will not scratch or otherwise damage the scope 58. Furthermore, as shown in FIG. 1, the support member 32 will aid in raising an end of the scope 58 such that the insertion end 60 of the scope 58 will be in the warming liquid at all times. This will aid in ensuring that the scope is warmed to the ideal or required temperature.

Figure 4:
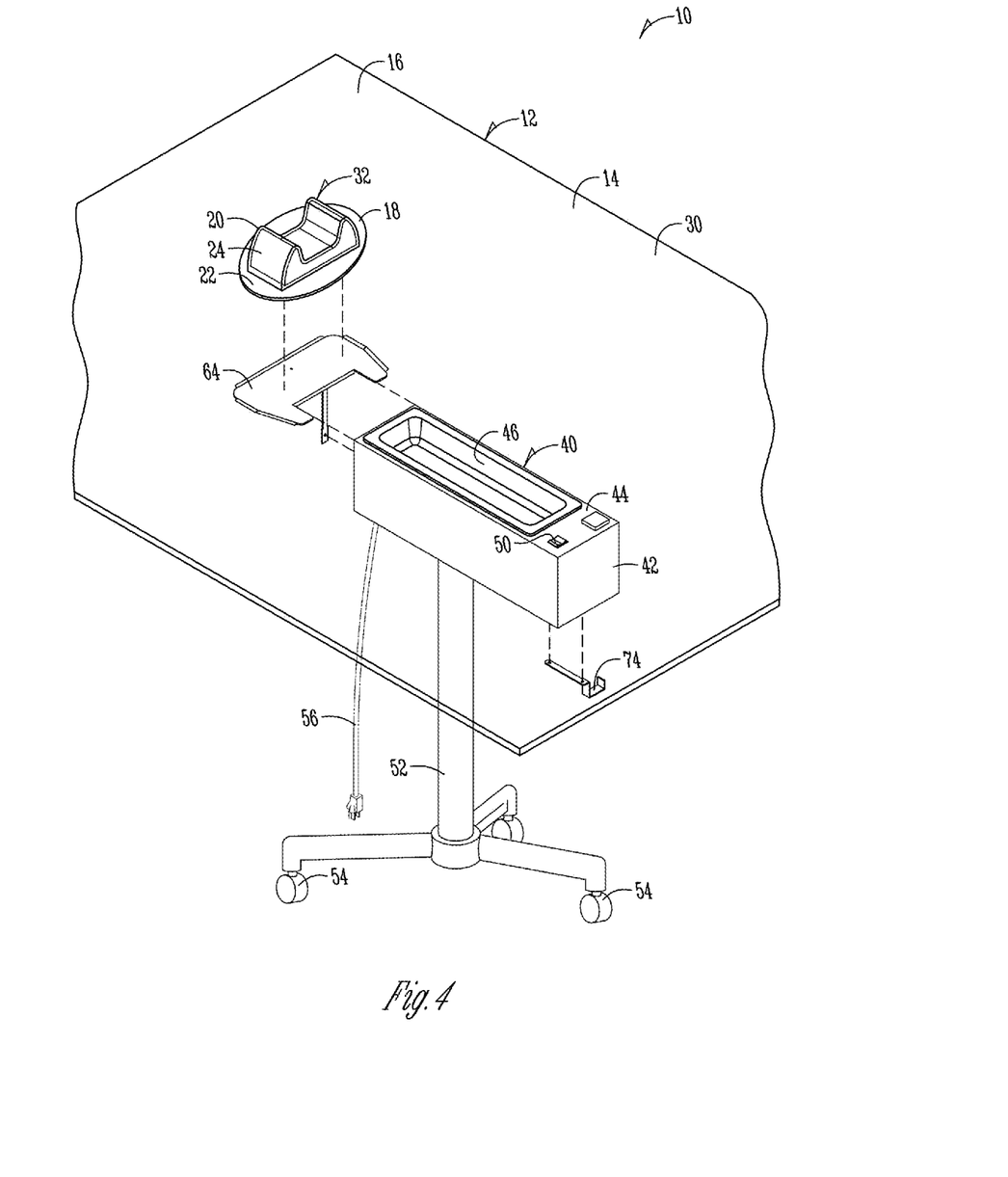
FIG. 4 is an exploded view of the device and system of FIG. 1.

As is also shown in FIGS. 1-4, an extension shelf 64 can be used with the present invention. The extension shelf 64 includes top and bottom surfaces 66, 68, and a support or attachment means 72 for attaching the shelf to the body 42 of the warming device 40. The support shelf may simply be screwed or otherwise adhered to body 42 of the warming device 40. The extension shelf 64 provides increased area to allow the support member to rest thereon during use of the pillow drape 12 of the present invention. As noted, the amount of space in a surgical or medical room is limited. Therefore, the extension shelf provides additional space for the warming device 40 and pillow drape 12, while not reducing the usable space in the medical room. The extension shelf 64 allows for an easy attachment to the warming device to provide support for the pillow drape 12, including the support member 32. Thus, as shown in FIG. 4, the support member 32 may rest or be positioned on the extension shelf 64 before placing the scope 58 in the warming device 40. Furthermore, while the extension shelf 64 of the present invention is shown to extend generally only at one side or end of the warming device 40, it is contemplated by the present invention that the extension shelf may be any size and configuration needed. For example, the extension shelf could extend from an end and along a side of the warming device 40 to provide additional space for medical personnel to place medical tools and other devices. The extension shelf may also be smaller, if the warming device 40 is smaller or support member 32 is smaller. This may be beneficial when the amount of available space is even less than ideal.

According to one embodiment of the present invention, the extension shelf 64 is positioned opposite the controls 50 of the warming device 40. Doing so aids in keeping the raised (optic) end 62 of the scope 58 away from the controls 50, such that adjusting the controls 50 will include a lower or reduced risk of altering the position of the scope 48, or accidentally knocking the scope 48 off of the device 40. However, as medical devices, such as the warming device 40 shown in the figures, include varying configurations and placements of controls and other information, the location of the extension shelf 64 and support member 32 need not be in the exact configuration shown in the Figures, and can be positioned adjacent the device to best increase space and reduce damage to the equipment.

Also shown in the Figures is a cord hook 74 attached to the warming device 40. As shown best in FIG. 2, a power cord 56 for the warming device 40 extends from an underside of the warming device 40. As the extension shelf 64 and support member 32 of the pillow drape 12 is positioned on the same side as the power cord 56, it may be desired to route the power cord 56 to the opposite side such that it can be out of the way for medical personnel. Therefore, the cord hook 74 can be attached to the underside of the warming device 40, and the power cord 56 can be routed under the warming device and through a router 78 of the hook 74 to route the cord away from the support member 32 side of the medical system 10. The cord hook 74 can be attached in any manner to the warming device 40. For example, the cord hook 74 can be screwed, glued, taped, or otherwise adhered to the warming device 40. In addition, while the cord hook 74 is shown to be attached to the underside of the warming device 40, it is contemplated that the hook can be placed or attached generally anywhere to the warming device 40 such that it is able to support the power cord 56. However, the location of the cord hook 74 as shown in the Figures is positioned such that the hook can be attached to the warming device using existing screw holes.

Figure 5:
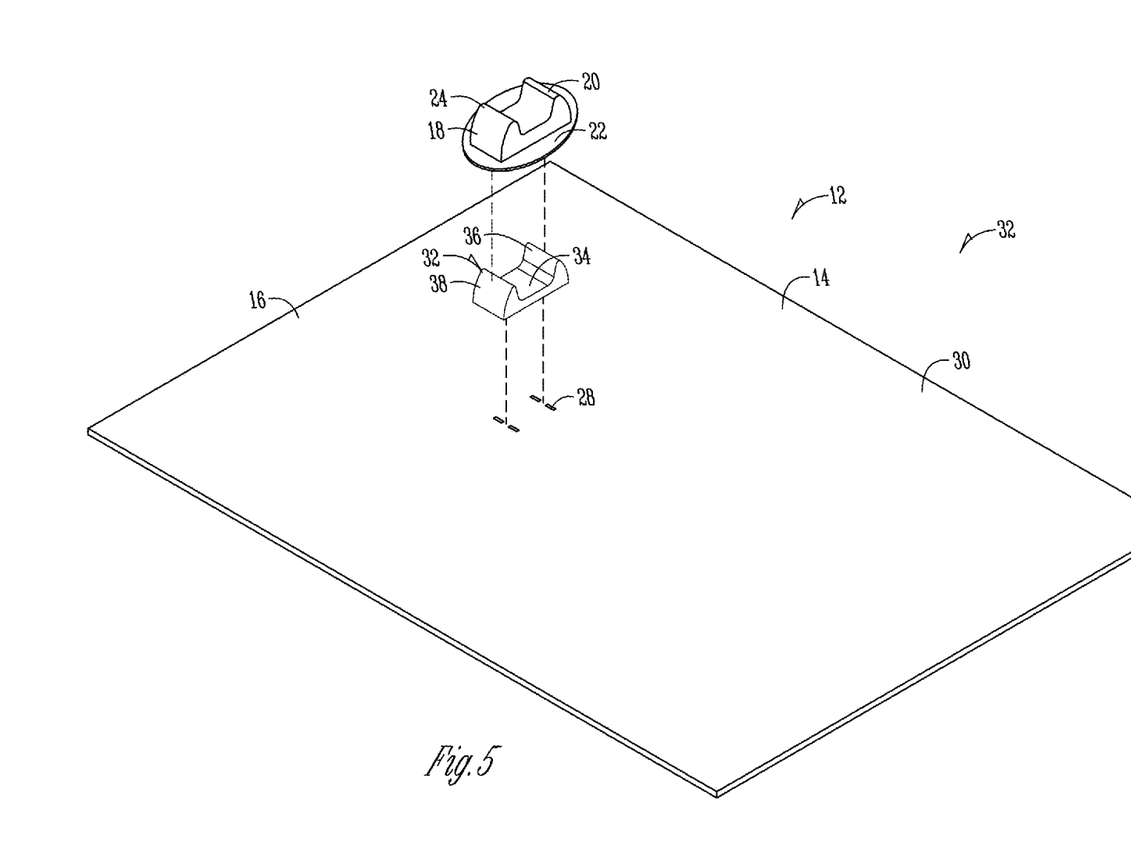
FIG. 5 is an exploded view of a pillow drape for use with the drape system according to an embodiment of the present invention.

FIG. 5 is an exploded view of the pillow drape 12 for use with the system 10 according to an embodiment of the present invention. As mentioned above, the pillow drape 12 can be comprised of a first section 16, including a sheet 14, and a second section 18, including a cover portion 20. As noted previously, the first section 16 or sheet 14 comprises a sterilized plastic, such as polyurethane. The sheet 14 may be opaque or also may be transparent. Slits 28 can be placed into the sheet at the location of the support member and second section 18, and can be used to aide in sterilizing the pillow drape 12, as will be described below. The support member 32 and second section 18 (cover section 20) are then positioned or attached to the sheet at the slits 28. As shown in FIG. 5, the second section 18 may include a cover portion 20 and a flange-type portion 22 to define a pocket 24 for housing the support member 32. While the cover portion 20 or pocket 24 shown in FIG. 5 is shown to be the same shape as a support member 32, the shape is for purposes of understanding, and is not to be limiting to the present invention. The cover portion 20 forming the pocket 24 can be any shape, including a simple dome shape that is able to conform to the shape of the support member 32. Furthermore, the second section 18 of the pillow drape 12 will also be formed of a sterilized plastic, such as polyurethane.

To form the pillow drape 12 of the present invention, the following method can be used. The desired size and shape of the support member 32, including the first surface 34, and first and second side walls 36, 38 is decided. The support member is then formed into the said shape, such as by cutting a piece of foam into the desired shape of the support member 32. A second section or sheet 18 of sterilized polyurethane can be positioned through a hole on a forming board with a flange portion 22 around the edge of the hole to aid in holding the second section in place. The support member 32 is then inserted into the now formed pocket 24 in the second section 18 in an upside down orientation. The first section 16 can then be placed on top of the support board with the slits 28 positioned adjacent the support member 32 and within the opening of the second section. The first and second sections 16, 18 can then be sealed to one another, such as melting, adhering, or the like, to connect the first and second portions to form a single pillow drape 12. The now formed pillow drape 12, including the first section 16, second section 20, and support member 32 can then be sterilized according to known sterilization processes. The location of the slits 28 adjacent to the support member will allow the sterilization process to sterilize the support member 32 within the pocket 24 between the first and second sheets 16, 18, along with the rest of the pillow drape 12. The pillow drape 12 can then be packaged and sent to be used with a warming device 40. In addition, the extension shelf 64 and cord hook 74 can be included with the pillow drape 12 to make the medical system 10 as shown in FIG. 1.

In addition, the pillow drape 12 can be formed in other manners as well. For example, the support member 32 could be molded or formed of a thicker piece of plastic, such a polyurethane, to include the support member 32 formed integrally with the first section 16 of the pillow drape 12. Thus, the integrally formed support member 32 would not be a separate piece from the rest of the pillow drape/sheet. Furthermore, the support member 32 could be formed of a material, such as a rubber or plastic, which could be sealed directly to the first sheet 16 of the pillow drape 12. Thus, this would eliminate the need of a second section 18 including a pocket 24. Furthermore, as noted previously, the size and configuration of the support member 32 can dictate the size of the pocket 24 between the first and second sheets 16, 18. The present invention is not to be limited to the configurations shown in the Figures, as well as the exact method described above.

Figure 6:
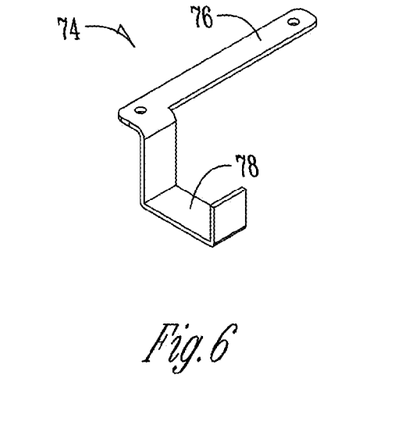
FIG. 6 is a perspective view of an extension shelf for use with the drape system according to an embodiment of the present invention.

FIG. 6 is a perspective view of the cord hook 74 according to an embodiment of the present invention. As noted, the cord hook 74 includes a hook attachment portion 76, and a router portion 78. The attachment portion 76 is used to attach the cord hook 74 to the body 42 of the warming device 40. The router portion 78 is used to hold a route the power cord 56 of the warming device 40. The configuration of the cord hook 74 is not to be limited by that shown in FIG. 6. For example, the router portion 78 may include an enclosed circle, or the addition of additional or a plurality of hooks to allow for the cord hook 74 to route a plurality of power cords for the warming device and any other medical device. Furthermore, as noted previously, while FIG. 6 shows that the cord hook 74 can be attached. by screws at the attachment portion 76 to the warming device 40, it is contemplated that the cord hook be attached to the warming device via other means. For example, the cord hook 74 could be attached via tape, via glue, via VELCRO®(hook and loops), or the like. The cord hook may comprise generally any rigid material, such as, but not limited to, metal, plastic, rubber, or the like.

Figure 7:
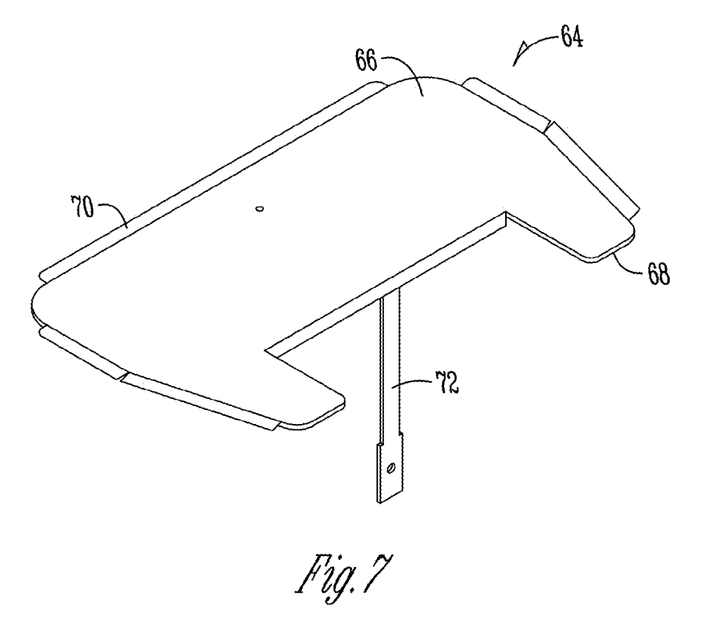
FIG. 7 is a perspective view of a cord hook for use with the drape system according to an embodiment of the present invention.

FIG. 7 is a perspective view of an embodiment of the extension shelf 64 according to the present invention. The extension shelf 64 shown in FIG. 7 includes a top surface 66 and an opposite bottom surface 68. The top surface is used to support and hold items in the medical room, such as the support member 32 of the pillow drape 12. However, the extension shelf could also be used to hold other medical instruments, such as scopes and other tools. Thus, the size and shape of the extension shelf can be configured to that configured to any configuration as needed. For example, as noted above, it is contemplated that the shelf extends along one end of the warming device, an end in a side of the warming device, an end in both sides of the warming device, or generally around all sides and ends of the warming device. The present invention is not to be limited by the configurations shown in the Figures. Also shown in FIG. 7 is a plurality of shelf lips 70 surrounding at least a portion of the extension shelf 64. The shelf lip 70 is included to aid in preventing items from falling off the extension shelf. Finally, a shelf support 72 is shown in FIG. 7. The shelf support 72 may also be known as a shelf attachment means.

Thus, it is contemplated that the shelf 64 may be attached to the warming device via the shelf support or attachment means 72. As shown in FIG. 7, the shelf can be screwed to the body 42 of the warming device 40. However, it is contemplated that other means will be used to attach the shelf to the warming device 40, such as, but not limited to, screws, VELCRO® (hook and loops), glue, adhesive, tape, or the like. The invention is not to be limited to the exact configuration and attachment means shown and described.

The foregoing description has been presented for purposes of illustration and description, and it not intended to be an exhaustive list or to limit the invention to precise forms disclosed. It is contemplated that other alternative processes obvious to those skilled in the art are considered to be included in the invention. The descriptions are merely examples of embodiments. For example, the materials of the various components described may be configured as required. For example, while the sheet has been described as being polyurethane, and the support member as a foam, it is contemplated that the sheet may be any other sterilized material or material used in the medical industry. The support member 32 may also be any material capable of supporting a medical instrument. Furthermore, the size of the pillow drape, including the excess 30 of the sheets, the size and configuration of the support members 32, as well as the size and configuration of the extension shelf may be adjusted as required or desired according to the use and need in the operating or other medical room. It is understood that any other modifications, substitutions, and/or additions may be made, which are within the intended spirit and scope of the invention. From the foregoing, it can be seen that present invention accomplishes at least all of the stated objectives.

What is claimed is:

1. A drape for use with a thermal medical treatment apparatus having a body including a recessed basin in a top surface, comprising:
    a first sheet for covering the recessed basin and body and hanging from the apparatus and including at least one aperture;
    a second sheet including portions of the second sheet sealed to the first sheet to form an integral unit with a pocket therebetween; and
    a support member housed in the pocket between the sheets for supporting a medical device adjacent the recessed basin;
    wherein the support member is housed within the pocket of the sheet such that the sheets and support member comprise the drape as an integral unit wherein the support member is substantially enclosed within the pocket such that the drape is placed on the apparatus in a ready to use manner; and
    wherein the at least one aperture allows for sterilizing the support member within the pocket.

2. The drape of claim 1 wherein the support member comprises a deformable material.

3. The drape of claim 2 wherein the support member comprises a foam material.

4. The drape of claim 1 wherein the pocket is shaped substantially similar to a shape of the support member.

5. The drape of claim 4 wherein the support member is housed in the pocket between the first and second sheets.

6. The drape of claim 1 wherein the support member comprises a first surface and first and second walls extending from the first surface.

7. The drape of claim 1 wherein the first and second sheets comprise sterilized polyurethane.

8. A drape for use with a thermal medical treatment apparatus having a body including a recessed basin in a top surface, comprising:
    a first sheet for covering the recessed basin and body and hanging from the apparatus;
    a second sheet attached to the first sheet to form a pocket therebetween;
    said second sheet including edges that are sealed to the first sheet to form the pocket; and
    a support member positioned in the pocket of the first and second sheets, the support member configured to support a medical device adjacent the recessed basin;
    wherein the support member is substantially enclosed within the pocket such that the drape is placed on the apparatus in a ready to use manner; and
    wherein the first or second sheets include at least one aperture to allow for sterilizing the support member within the pocket.

9. The drape of claim 8 wherein the support member comprises a first surface and first and second walls extending from the first surface.

10. The drape of claim 9 wherein the support member comprises a deformable material.

11. The drape of claim 10 wherein the support member comprises foam.

12. The drape of claim 8 wherein the second sheet comprises a cover portion and a flange portion extending at least partially around an open end of the cover portion.

13. The drape of claim 12 wherein the second sheet is sealed to the first sheet at the flange portion of the second sheet.

14. A system for covering a thermal medical treatment apparatus having a body including a recessed basin in a top surface, comprising:

- an extension shelf attached to the apparatus body adjacent the recessed basin;
- a drape covering the extension shelf, recessed basin, and apparatus body and hanging therefrom, the drape including at least one aperture;
- said drape comprising a first sheet for covering the recessed basin and body and hanging from the apparatus, and a second sheet including portions of the second sheet sealed to the first sheet to form an integral unit with a pocket therebetween; and
- a support member housed substantially in the pocket of the drape and positioned on the extension shelf with the first sheet between the support member and shelf for supporting a medical device adjacent the recessed basin;
- wherein the support member is housed within a pocket of the sheet that is shaped substantially similar to the support member such that the sheet and support member comprise the drape as an integral and ready to use unit; and
- wherein the at least one aperture allows for sterilizing the support member within the pocket.

15. The system of claim 14 further comprising a cord hook attached to the apparatus body and configured to hold and route a power cord for the apparatus.

16. The system of claim 14 wherein the extension shelf extends from one side of the apparatus.

17. The system of claim 14 wherein the extension shelf extends from a plurality of sides of the apparatus.

18. The system of claim 14 wherein the support member comprises a first surface and first and second walls extending from the first surface.

\* \* \* \* \*